United States Patent
Choi et al.

(10) Patent No.: US 11,911,134 B2
(45) Date of Patent: Feb. 27, 2024

(54) APPARATUS AND METHOD FOR ESTIMATING BIO-INFORMATION

(71) Applicant: SAMSUNG ELECTRONICS CO., LTD., Suwon-si (KR)

(72) Inventors: Jin Woo Choi, Suwon-si (KR); Sang Yun Park, Hwaseong-si (KR); Hye Rim Lim, Suwon-si (KR); Jae Min Kang, Seoul (KR); Seung Woo Noh, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 534 days.

(21) Appl. No.: 17/133,093

(22) Filed: Dec. 23, 2020

(65) Prior Publication Data

US 2022/0022757 A1    Jan. 27, 2022

(30) Foreign Application Priority Data

Jul. 23, 2020 (KR) .................. 10-2020-0091506

(51) Int. Cl.
*A61B 5/0205* (2006.01)
*A61B 5/00* (2006.01)
(Continued)

(52) U.S. Cl.
CPC ............ *A61B 5/0205* (2013.01); *A61B 5/004* (2013.01); *A61B 5/0082* (2013.01);
(Continued)

(58) Field of Classification Search
CPC . A61B 5/02433; A61B 5/02438; A61B 5/681; A61B 5/7207; A61B 5/7221; A61B 5/721; A61B 5/02416; A61B 5/7214; A61B 5/0261; A61B 5/7253; A61B 5/02108; A61B 5/0205; A61B 5/004; A61B 5/0082; A61B 5/0095; A61B 5/02007; A61B 5/055; A61B 5/489; A61B 2562/0247; A61B 5/1172; A61B 5/14552; A61B 5/02116;
(Continued)

(56) References Cited

U.S. PATENT DOCUMENTS 8,086,301 B2   12/2011   Cho et al.
9,089,306 B2   7/2015    Harada et al.
(Continued)

FOREIGN PATENT DOCUMENTS

JP         5014051 B2     8/2012
KR    10-0871230 B1    11/2008
(Continued)

*Primary Examiner* — Eric F Winakur
*Assistant Examiner* — Elina Sohyun Ahn
(74) *Attorney, Agent, or Firm* — Sughrue Mion, PLLC

(57) ABSTRACT

An apparatus for non-invasively measuring bio-information is provided. The apparatus for estimating bio-information may include a pulse wave sensor configured to measure a pulse wave signal from an object; a sensor position sensor configured to obtain sensor position information of the pulse wave sensor with respect to the object, based on the object being in contact with the pulse wave sensor; and a processor configured to estimate the bio-information based on blood vessel position information of the object, the sensor position information, and the pulse wave signal.

19 Claims, 12 Drawing Sheets

(51) Int. Cl.
    *A61B 5/055*     (2006.01)
    *A61B 5/02*     (2006.01)
    *A61B 5/16*     (2006.01)
    *A61B 8/08*     (2006.01)
    *A61B 5/1172*     (2016.01)
    *A61B 5/021*     (2006.01)

(52) U.S. Cl.
    CPC ........ *A61B 5/0095* (2013.01); *A61B 5/02007* (2013.01); *A61B 5/055* (2013.01); *A61B 5/165* (2013.01); *A61B 5/442* (2013.01); *A61B 5/489* (2013.01); *A61B 8/085* (2013.01); *A61B 5/02108* (2013.01); *A61B 5/1172* (2013.01); *A61B 2562/0247* (2013.01)

(58) Field of Classification Search
    CPC ... A61B 5/02125; A61B 5/117; A61B 5/6843; A61B 5/0053; A61B 5/022; A61B 5/6826; A61B 5/6898; A61B 2090/065; A61B 2562/02; A61B 5/7282; A61B 8/06; A61B 5/021; A61B 8/04; A61B 5/14551; G06V 40/14; G06V 40/1312
See application file for complete search history.

(56) References Cited

U.S. PATENT DOCUMENTS

| | | | |
|---|---|---|---|
| 10,398,324 B2 | 9/2019 | Mukkamala et al. | |
| 2016/0089042 A1 | 3/2016 | Saponas et al. | |
| 2016/0106325 A1* | 4/2016 | Kang ................... | A61B 5/0261 600/479 |
| 2017/0095171 A1* | 4/2017 | Park .................... | A61B 5/7475 |
| 2017/0251935 A1 | 9/2017 | Yuen | |
| 2018/0177413 A1* | 6/2018 | Kwon .................. | A61B 5/6898 |
| 2018/0310841 A1 | 11/2018 | Khwaja et al. | |
| 2018/0310842 A1 | 11/2018 | Khwaja et al. | |
| 2018/0314879 A1 | 11/2018 | Khwaja et al. | |
| 2019/0076032 A1 | 3/2019 | Park et al. | |
| 2019/0313979 A1 | 10/2019 | Kang et al. | |

FOREIGN PATENT DOCUMENTS

| | | |
|---|---|---|
| KR | 10-2019-0030152 A | 3/2019 |
| KR | 10-2019-0088784 A | 7/2019 |
| KR | 10-2019-0119414 A | 10/2019 |
| KR | 10-2019-0137893 A | 12/2019 |
| WO | 2018014870 A1 | 1/2018 |
| WO | 2018229587 A1 | 12/2018 |
| WO | 2020006518 A1 | 1/2020 |

\* cited by examiner

APPARATUS AND METHOD FOR ESTIMATING BIO-INFORMATION

CROSS-REFERENCE TO RELATED APPLICATION(S)

This application is based on and claims priority under 35 U.S.C. § 119 to Korean Patent Application No. 10-2020-0091506, filed on Jul. 23, 2020, in the Korean Intellectual Property Office, the disclosure of which is incorporated by reference herein in its entirety.

BACKGROUND

1. Field

The following description relates to an apparatus and method for estimating bio-information, and technology for cuffless blood pressure estimation.

2. Description of Related Art

General techniques for extracting cardiovascular characteristics, such as blood pressure, and the like, without using a pressure cuff include a pulse transit time (PIT) method and a pulse wave analysis (PWA) method.

The pulse transit time (PTT) method is a method of extracting cardiovascular characteristics by analyzing the shape of a photoplethysmography (PPG) signal or a body surface pressure signal obtained from a peripheral part of the body, e.g., a fingertip, a radial artery, or the like. The blood ejected from the left ventricle causes reflection at areas of large branches, such as the renal arteries and the iliac arteries, and the reflection affects the shape of the pulse wave or body pressure wave measured at the peripheral part of the body. Thus, by analyzing this shape, arterial stiffness, arterial age, aortic artery pressure waveform of the like can be inferred.

The PWA method is a method of extracting cardiovascular characteristics, such as arterial stiffness, blood pressure, or the like, by measuring a pulse wave transmission time. In this method, a delay (a PTT) between an R-peak (left ventricular contraction interval) of an electrocardiogram (ECG) and a peak of a PPG signal of a finger or the radial artery is measured by measuring the ECG and PPG signals of the peripheral part of the body and by calculating a velocity at which the blood from the heart reaches the peripheral part of the body by dividing an approximate length of the arm by the PTT.

SUMMARY

Additional aspects will be set forth in part in the description which follows and, in part, will be apparent from the description, or may be learned by practice of the presented embodiments.

According to an aspect of an example embodiment, an apparatus for estimating bio-information may include a pulse wave sensor configured to measure a pulse wave signal from an object; a sensor position sensor configured to obtain sensor position information of the pulse wave sensor with respect to the object, based on the object being in contact with the pulse wave sensor; and a processor configured to estimate the bio-information based on blood vessel position information of the object, the sensor position information, and the pulse wave signal.

The sensor position sensor may be configured to obtain the sensor position information based on an image of the object, or a fingerprint image.

The apparatus may include a blood vessel position sensor configured to obtain the blood vessel position information of the object based on a user input and at least one of an optical image, an ultrasonic image, a magnetic resonance imaging (MRI) image, and a photoacoustic image of the object.

The processor may be configured to control an output interface to guide a user to place the pulse wave sensor at a blood vessel position of the object based on the blood vessel position information of the object and the sensor position information.

The pulse wave sensor may have a plurality of channels to measure pulse wave signals at a plurality of points of the object, and the pulse wave sensor may be configured to obtain the pulse wave signal for estimating the bio-information by driving at least one of the plurality of channels based on the blood vessel position information of the object and the sensor position information.

The processor may be configured to determine a channel from among the plurality of channels, which is located closest to a blood vessel position, or a channel which is located within a predetermined distance from the blood vessel position, as the channel to be driven.

In response to determining that no channel is located within the predetermined distance from the blood vessel position, the processor is further configured to control an output interface to guide a user to change a contact position of the object.

The pulse wave sensor may have a plurality of channels to measure a plurality of pulse wave signals at a plurality of different points of the object or in a predetermined area of the object, and the processor may be configured to select at least one pulse wave signal for estimating the bio-information from among the plurality of pulse wave signals, based on the blood vessel position information of the object and the sensor position information.

The processor may be configured to select the at least one pulse wave signal of a channel which is located closest to the blood vessel position, or the at least one pulse wave signal of a channel which is located within a predetermined distance from the blood vessel position.

The apparatus may include a force sensor configured to measure a force applied by the object to the pulse wave sensor, or a pressure sensor configured to measure pressure applied by the object to the pulse wave sensor.

The processor may be configured to estimate the bio-information based on the pulse wave signal, measured by the pulse wave sensor, and the force measured by the force sensor or the pressure measured by the pressure sensor.

The bio-information may be one or more of blood pressure, vascular age, arterial stiffness, aortic pressure waveform, vascular compliance, stress index, fatigue level, skin age, and skin elasticity.

According to an aspect of an example embodiment, a method of estimating bio-information may include, based on an object being in contact with a pulse wave sensor, obtaining sensor position information of the pulse wave sensor with respect to the object; driving the pulse wave sensor to measure a pulse wave signal from the object; and estimating the bio-information based on blood vessel position information of the object, the sensor position information, and the pulse wave signal.

The obtaining of the sensor position information may include obtaining an image of the object by an image sensor based on the object being in contact with the pulse wave sensor, and obtaining the sensor position information based on the image of the object.

The method may include obtaining the blood vessel position information of the object based on at least one of an ultrasonic image, a magnetic resonance imaging (MRI) image, and a photoacoustic image of the object.

The method may include measuring a force applied by the object to the pulse wave sensor, or a pressure applied by the object to the pulse wave sensor.

The estimating of the bio-information may include estimating the bio-information based on the pulse wave signal, measured by the pulse wave sensor, and the force measured by a force sensor or the pressure measured by a pressure sensor.

The method may include controlling an output interface to guide a user to place the pulse wave sensor at a blood vessel position of the object based on the blood vessel position information of the object and the sensor position information.

The method may include, in response to a plurality of pulse wave signals being measured at a plurality of points of the object or in a predetermined area of the object, selecting at least one of the plurality of pulse wave signals based on the blood vessel position information of the object and the sensor position information.

The selecting of the at least one of the plurality of pulse wave signals may include selecting the at least one of the plurality of pulse wave signals of a channel, which is located closest to the blood vessel position, or the at least one of the plurality of pulse wave signals of a channel which is located within a predetermined distance from the blood vessel position, as the pulse wave signal.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1A:
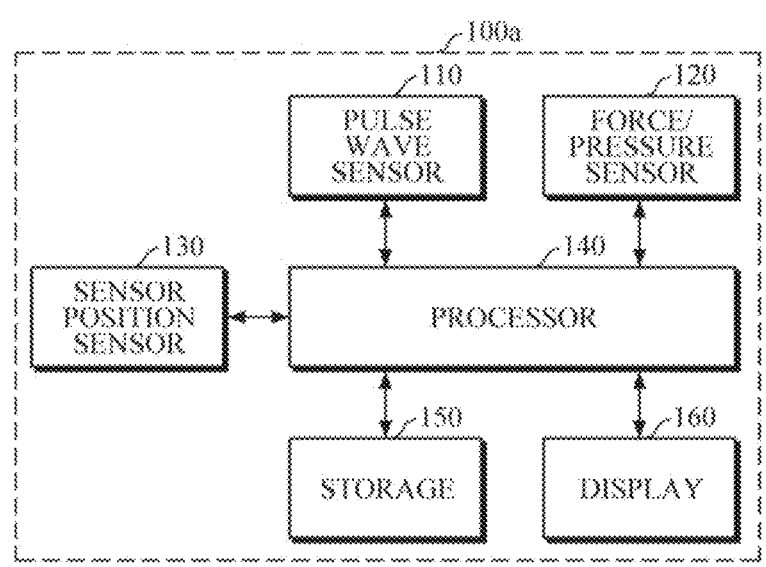
FIGS. 1A and 1B are block diagrams illustrating an apparatus for estimating bio-information according to embodiments of the present disclosure.

Details of other embodiments are included in the following detailed description and drawings. Advantages and features of the present disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms "first," "second." etc. may be used herein to describe various elements, these elements should not be limited by these terms. These terms are only used to distinguish one element from another. Also, the singular forms of terms are intended to include the plural forms of the terms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and the unit may be implemented by using hardware, software, or a combination thereof.

Hereinafter, embodiments of an apparatus and method for estimating bio-information will be described in detail with reference to the accompanying drawings.

Figure 1B:
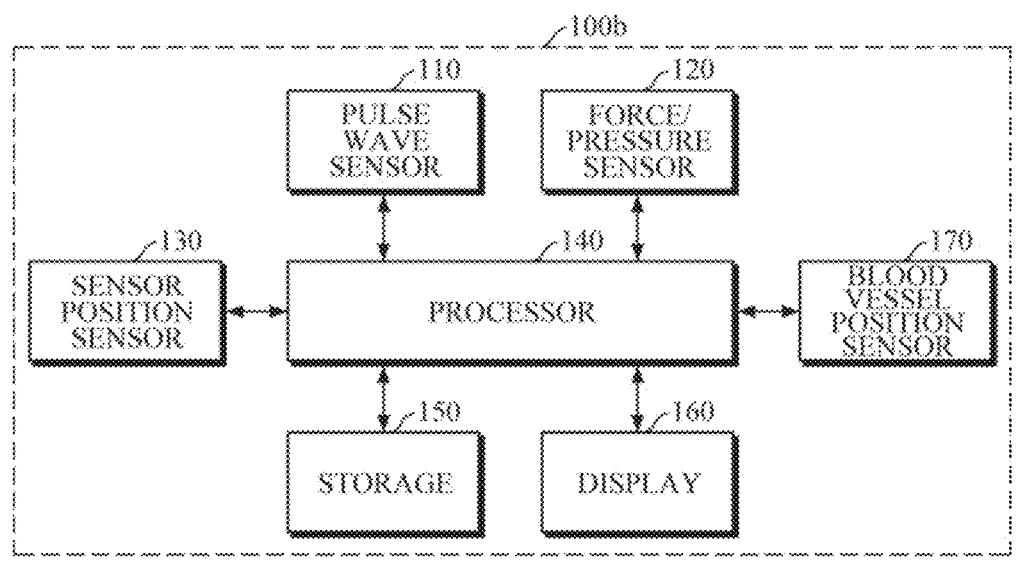

FIGS. 1A and 1B are block diagrams illustrating an apparatus for estimating bio-information according to embodiments of the present disclosure.

The apparatuses 100a and 100b for estimating bio-information according to embodiments of the present disclosure may be mounted in terminals, such as a smart phone, a tablet personal computer (PC), a desktop computer, a laptop computer, etc., wearable devices, and the like. In this case, examples of the wearable devices may include a wristwatch-type wearable device, a bracelet-type wearable device, a wristband-type wearable device, a ring-type wearable device, a glasses-type wearable device, a headband-type wearable device, etc., but the wearable devices are not limited thereto.

Referring to FIG. 1A, the apparatus 100a for estimating bio-information includes a pulse wave sensor 110, a force/pressure sensor 120, a sensor position sensor 130, a processor 140, a storage 150, and a display 160.

The pulse wave sensor 110 measures a PPG signal (hereinafter referred to as a "pulse wave signal") from an object. In this case, the object may be a body area which may come into contact with the pulse wave sensor 110, and may be a body part at which pulse waves may be easily measured based on PPG signals. For example, the object may be a finger where blood vessels are densely located, but the object is not limited thereto and may be an area on the wrist that is adjacent to the radial artery, or a peripheral part of the body, such as an upper portion of the wrist, toes, etc., where veins or capillaries are located.

The pulse wave sensor 110 may include one or more light sources for emitting light onto the object, and one or more light receivers which are disposed at positions spaced apart from the light sources by a predetermined distance and detect light scattered or reflected from the object. The light sources may emit light of different wavelengths. For example, the light sources may emit light of an infrared wavelength, a green wavelength, a blue wavelength, a red wavelength, a white wavelength, and the like. The light sources may include a light emitting diode (LED), a laser diode (LD), a phosphor, etc., but are not limited thereto. Further, the light receivers may include a photodiode, a photodiode array, a complementary metal-oxide semiconductor (CMOS) image sensor, a charge-coupled device (CCD) image sensor, and the like.

The pulse wave sensor 110 may have a single channel including a light source and a light receiver, so as to measure a pulse wave signal at a specific point of the object. Alternatively, the pulse wave sensor 110 may have multiple channels to measure a plurality of pulse wave signals at multiple points of the object. Each of the channels of the pulse wave sensor 110 may be formed in a pre-defined shape such as a circular shape, an oval shape, a fan shape, etc., so that pulse wave signals may be measured at multiple points of the object. Each channel of the pulse wave sensor 110 may include one or more light sources and one or more light receivers. Further, each channel may include two or more light sources to emit light of a plurality of wavelengths. Alternatively, the pulse wave sensor 110 may be configured to measure a plurality of pulse wave signals in a predetermined area of the object. For example, the pulse wave sensor 110 may include one or more light sources, and a light receiver formed as a CMOS image sensor and disposed at a predetermined distance from the one or more light sources.

When a user places an object on the pulse wave sensor 110 and increases or decreases a pressing force/pressure to induce a change in pulse wave amplitude, the force/pressure sensor 120 may measure the force/pressure exerted between the pulse wave sensor 110 and the object. The force/pressure sensor 120 may include a force sensor including a strain gauge, and the like, a force sensor array, an air bladder type pressure sensor, a pressure sensor in combination with a force sensor and an area sensor, and the like.

When the object is in contact with the pulse wave sensor 110, the sensor position sensor 130 may obtain a position on the object, being in contact with the pulse wave sensor 110, with respect to the pulse wave sensor 110 as sensor position information. One or more functions of the sensor position sensor 130 may be integrated with the processor 140.

For example, the sensor position sensor 130 may obtain the sensor position information based on object images captured by an external image capturing device. The external image capturing device may be a camera module installed at a fixed location or a camera module mounted in a mobile device such as a smartphone, and the like. For example, once the external image capturing device captures an image of the finger being in contact with the pulse wave sensor 110, the sensor position sensor 130 may receive the image of the finger through a communication module mounted in the apparatus 100a for estimating bio-information. By analyzing relative positions of the pulse wave sensor 110 and the finger based on the image of the finger, the sensor position sensor 130 may obtain the position of the finger, being in contact with the pulse wave sensor 110, as a sensor position. Further, if the external image capturing device, having the function of obtaining a sensor position, obtains sensor position information by capturing an image of the finger, the sensor position sensor 130 may receive the sensor position information from the external image capturing device through the communication module.

In this case, the communication module may communicate with the external device by using various wireless or wired communication techniques, such as Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, mobile communication, and the like. However, this is merely exemplary and is not intended to be limiting.

In another example, the sensor position sensor 130 may include a fingerprint sensor for acquiring a fingerprint image of the object being in contact with the pulse wave sensor 110. The fingerprint sensor may be disposed at an upper end or a lower end of the pulse wave sensor 110. The sensor position sensor 130 may estimate a sensor position by analyzing a change in fingerprint pattern based on the fingerprint image of the object. For example, when a finger applies pressure to the pulse wave sensor 110, a contact position of the finger, which is in contact with the pulse wave sensor 110, is pressed more than other positions of the finger, such that a distance between ridges or valleys of a fingerprint at the contact position between the finger and the pulse wave sensor 110 is larger than other positions. If a distance between ridges or valleys of the fingerprint at a predetermined position of the finger is greater than or equal to a predetermined threshold value when compared to other positions, the sensor position sensor 130 may obtain the position as a sensor position.

The processor 140 may estimate bio-information based on the pulse wave signal obtained by the pulse wave sensor 110, the force/pressure obtained by the force/pressure sensor 120, the sensor position information obtained by the sensor position sensor 130, and blood vessel position information of the object. In this case, the bio-information may include blood pressure, vascular age, arterial stiffness, aortic pressure waveform, skin elasticity, skin age, stress index, fatigue level, etc., but is not limited thereto.

For example, the processor 140 may control an output interface to provide information that guides a user on a contact position of the object based on a blood vessel position of the object and sensor position. Further, if the pulse wave sensor 110 has multiple channels to measure a plurality of pulse wave signals at multiple points of the object, the processor 140 may select a proper channel based on the blood vessel position of the object and the sensor position, and may estimate bio-information by using the pulse wave signals measured by the determined channel.

For example, the processor 140 may generate an oscillogram based on the pulse wave signal obtained by the pulse wave sensor 110 and the force/pressure obtained by the force/pressure sensor 120, and may estimate bio-information by using the generated oscillogram. In this case, once the force/pressure sensor 120 measures a contact force between the object and the pulse wave sensor 110, the processor 140 may convert the contact force into contact pressure by using a conversion model which defines a correlation between the contact force and the contact pressure. Alternatively, the processor 140 may obtain contact pressure by using the contact force and area information of the pulse wave sensor 110. Furthermore, if the force/pressure sensor 120 is implemented as a force sensor for measuring a contact force and an area sensor for measuring a contact area, the processor 140 may obtain contact pressure based on the contact force, measured by the force sensor, and the contact area measured by the area sensor.

The storage 150 may store a variety of information for estimating bio-information. For example, the storage 150 may store the pulse wave signals measured by the pulse wave sensor 110, the force/pressure obtained by the force/pressure sensor 120, the object images, fingerprint images, and sensor position information which are obtained by the sensor position sensor 130, and the like. Further, the storage 150 may store processing results of the processor 140, e.g., an estimated bio-information value. In addition, the storage 150 may store blood vessel position information pre-defined for each object of a user, and each user's characteristics information such as a user's age, gender, health condition, and the like. However, the information is not limited thereto.

The storage 150 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The display 160 may visually display the pulse wave signals measured by the pulse wave sensor 110, the force/pressure measured by the force/pressure sensor 120, and/or the processing results of the processor 140. While visually displaying the processing results of the processor 140, the display 160 may also provide a user with the information in a non-visual manner using a speaker, a haptic device, and the like. The display 160 may include a display module which includes a touch screen for receiving a user's touch input. Based on receiving a user's touch input, the display 160 may transmit the touch input to the processor 140.

For example, the display 160 may output the measured pulse wave signal in the form of graphs. Further, the display 160 may visually display an estimated blood pressure value of a user by using various visual methods, such as changing color, line thickness, font, and the like, based on whether the estimated blood pressure value falls within or outside a normal range. Alternatively, based on comparing the estimated blood pressure value with a previous estimation history, if it is determined that the estimated blood pressure value is abnormal, the display 160 may provide a warning message, and the like, as well as guide information on a user's action such as food information that the user should be careful about, related hospital information, and the like.

In addition, the display 160 may display information for guiding a user on a contact position of the object under the control of the processor 140. For example, the display 160 may display an image of the object, and may display a marker indicating a blood vessel position of the object and a marker indicating a sensor position, on the image of the object.

Referring to FIG. 1B, the apparatus 100b for estimating bio-information includes the pulse wave sensor 110, the force/pressure sensor 120, the sensor position sensor 130, the processor 140, the storage 150, the display 160, and a blood vessel position sensor 170. The pulse wave sensor 110, the force/pressure sensor 120, the sensor position sensor 130, the processor 140, the storage 150, and the display 160 are described above with reference to FIG. 1A, such that redundant descriptions thereof will be omitted.

The blood vessel position sensor 170 may obtain blood vessel position information of an object during a registration or initial calibration process. Alternatively, in response to a user's request for estimating bio-information, the blood vessel position sensor 170 may determine whether there is blood vessel position information of the object of the user or whether it is time to calibrate the information; and if there is no blood vessel position information of the object or it is time to calibrate the information, the blood vessel position sensor 170 may obtain blood vessel position information of the object from the user. One or more functions of the blood vessel position sensor 170 may be integrated with the processor 140.

For example, the blood vessel position sensor 170 may directly receive input of blood vessel position information from a user. In this case, the blood vessel position sensor 170 may display an image of an object on the display 160, and may provide an interface for the user to directly designate a blood vessel position on the object image by using an input means (e.g., finger, touch pen, etc.).

As another example, the blood vessel position sensor 170 may receive an image, which is captured by an external image capturing device for capturing an optical image, an ultrasonic image, a magnetic resonance imaging (MRI) image, a photoacoustic image, etc., through the communication module, and may obtain blood vessel position information of the object by analyzing the received image. Alternatively, if the external image capturing device may analyze a blood vessel position while capturing the image, the blood vessel position sensor 170 may receive the blood vessel position information of the object from the external image capturing device through the communication module.

In yet another example, the blood vessel position sensor 170 may include, for example, an ultrasonic sensor. The blood vessel position sensor 170 may obtain blood vessel position information by operating the ultrasonic sensor, which transmits an ultrasonic wave to the object, and receives a reflection wave from the object.

Figure 2A:
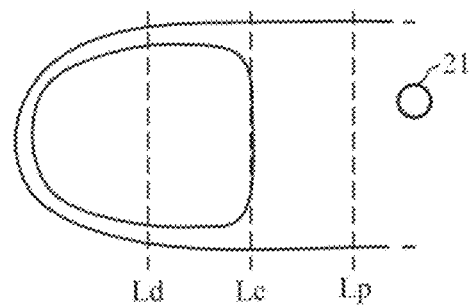
FIGS. 2A and 2B are diagrams illustrating a change in mean arterial pressure (MAP) according to a measurement position of a finger.
Figure 2B:
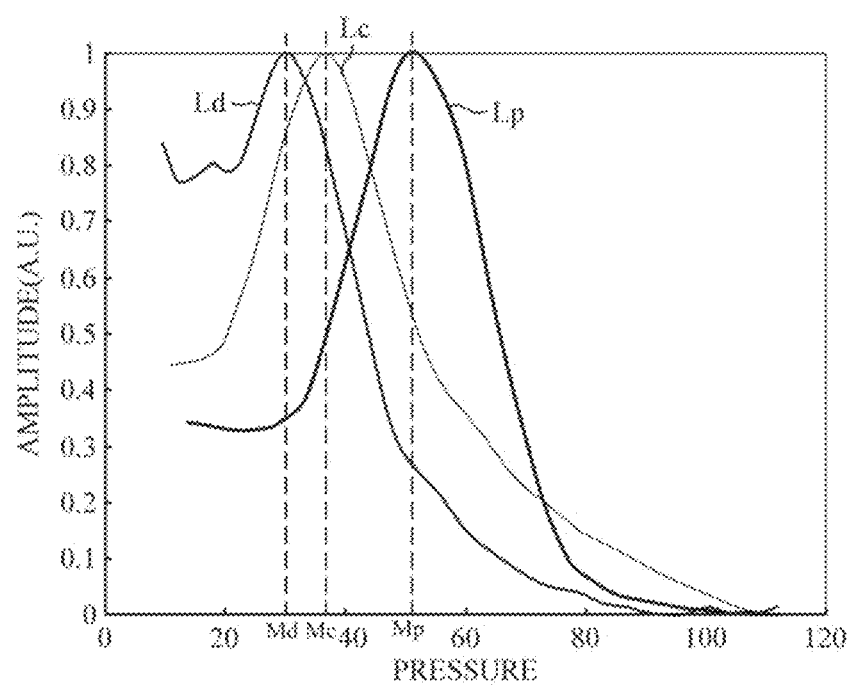
Figure 3A:
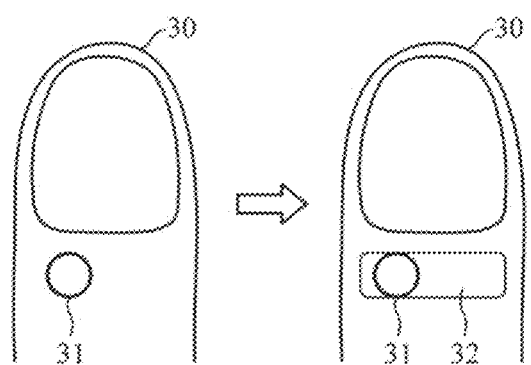
FIGS. 3A to 3C are diagrams explaining an example of estimating blood pressure based on blood vessel position information.
Figure 3B:
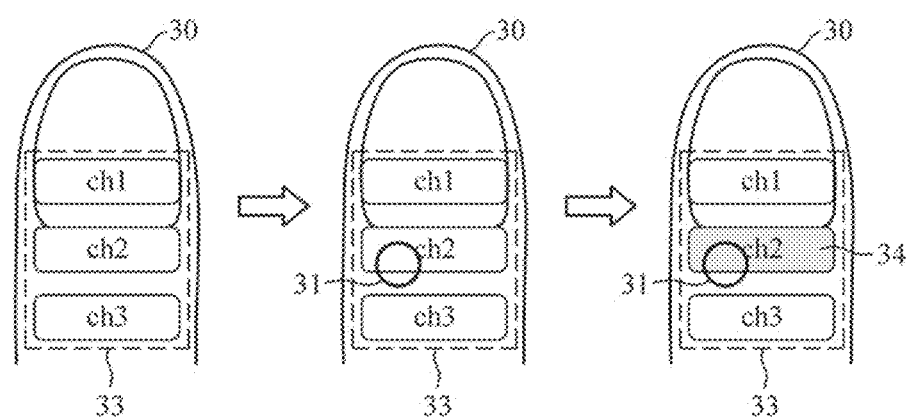
Figure 3C:
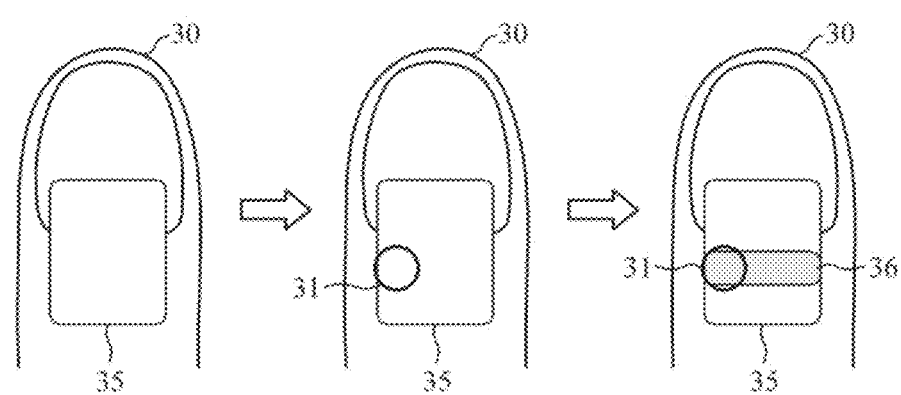
Figure 4A:
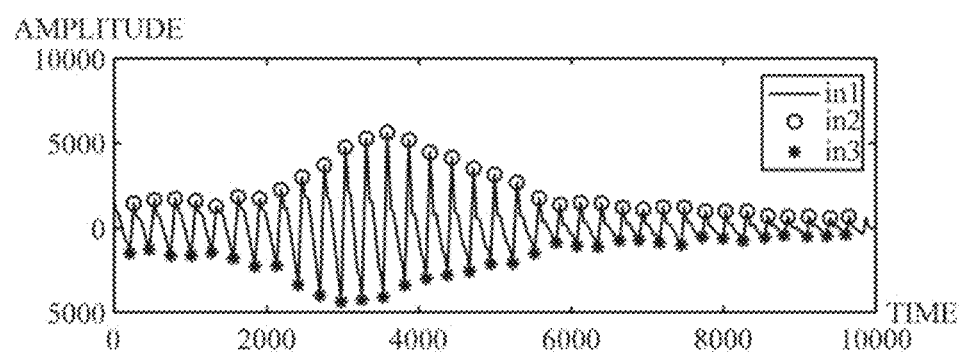
FIGS. 4A and 4B are diagrams explaining an example of estimating blood pressure using oscillometry.
Figure 4B:
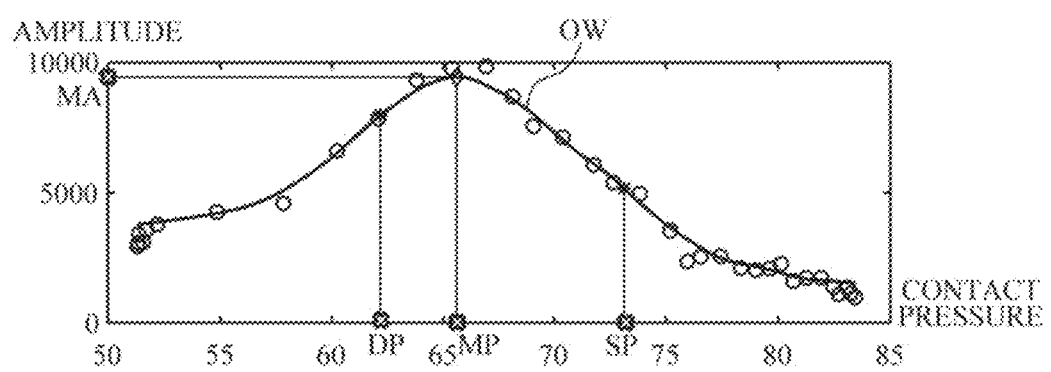

FIGS. 2A and 2B are diagrams illustrating a change in mean arterial pressure (MAP) according to a measurement position of a finger. FIGS. 3A to 3C are diagrams explaining an example of estimating blood pressure based on blood vessel position information. FIGS. 4A and 4B are diagrams explaining an example of estimating blood pressure using oscillometry.

Referring to FIGS. 1A to 4B, examples of estimating blood pressure will be described below.

FIG. 2A is a diagram illustrating a finger image in which a blood vessel position 21 and sensor positions Ld, Lc, and Lp are displayed on the finger image. FIG. 2B is a diagram illustrating a change in estimated MAP values Md, Mc, and Mp according to a change in the sensor positions Ld, Lc, and Lp relative to the blood vessel position 21. Generally, a method of measuring blood pressure by finger oscillometry includes constricting or dilating blood vessels by gradually increasing or decreasing pressure while the finger is in contact with the pulse wave sensor 110, and measuring blood pressure using an oscillometric pulse wave signal measured during this process. In this case, if a sensor position deviates from a blood vessel position while pressure applied to the finger increases or decreases, force/pressure for measuring finger oscillometry may not be applied properly to the arteries, thereby causing an error in estimating blood pressure.

FIG. 3A is a diagram explaining an example of the pulse wave sensor 110 having a single channel 32. The single channel 32 may include one light source and one light receiver. As described above, the processor 140 may display an image of a finger 30 on the display 160, and may control an output interface to provide information that guides a user to place a blood vessel position 31 of the finger on a position of the channel 32 of the pulse wave sensor 110.

FIG. 3B is a diagram explaining an example of the pulse wave sensor 110 having multiple channels 33 so as to measure pulse wave signals at multiple points of the finger 30. Each of the channels ch1, ch2, and ch3 may include a light source and a light receiver.

For example, based on receiving a request for estimating blood pressure, the processor 140 may select at least one of the multiple channels 33 by using the blood vessel position 31 of the finger 30 and sensor position information, and may drive the selected channel. For example, the processor 140 may select a channel ch2, which is located closest to the blood vessel position 31, from among the channels ch1, ch2, and ch3 of the pulse wave sensor 110, as the channel 34 to be driven. Alternatively, the processor 140 may drive a channel located within a predetermined distance from the blood vessel position 31. In this case, if there is no channel located within the predetermined distance from the blood vessel position 31, the processor 140 may control an output interface to provide information that guides a user to change a contact position of the finger based on the sensor position information and the blood vessel position information.

The processor 140 may estimate blood pressure by using the pulse wave signal measured by the driven channel 34. In this case, if a plurality of pulse wave signals are obtained by driving two or more channels, the processor 140 may obtain an estimated blood pressure value based on a combination of the pulse wave signals (e.g., difference of the pulse wave signals, difference of second-order differential signals, etc.), a combination of oscillograms (e.g., difference of oscillograms) obtained from each pulse wave signal, or a statistical value of blood pressure values estimated using each oscillogram.

As another example, the processor 140 may obtain pulse wave signals from each of the channels ch1, ch2, and ch3 by simultaneously or sequentially driving the multiple channels 33 of the pulse wave sensor 110, and may estimate blood pressure by using a pulse wave signal of the channel ch2, which is located closest to the blood vessel position 31, or a pulse wave signal of a channel which is located within a predetermined distance from the blood vessel position 31.

FIG. 3C is a diagram explaining an example of the pulse wave sensor 110 having multiple channels 35 to simultaneously measure a plurality of pulse wave signals in a predetermined area of the finger 30. For example, the multiple channels 35 may include light sources disposed at predetermined positions, and a plurality of detector arrays or CMOS image sensors disposed at predetermined distances from the light sources. The processor 140 may estimate blood pressure by using a pulse wave signal measured by a channel 36, which is located closest to the blood vessel position 31, or a pulse wave signal measured by a channel located within a predetermined distance from the blood vessel position 31, among the plurality of pulse wave signals measured by the multiple channels 35.

FIGS. 4A and 4B are diagrams explaining an example of estimating blood pressure based on oscillometry using a pulse wave signal and force/pressure.

Referring to FIGS. 4A and 4B, the processor 140 may extract, e.g., a peak-to-peak point of the pulse wave signal waveform by subtracting a negative (−) amplitude value in3 from a positive (+) amplitude value in2 of a waveform envelope in1 at each measurement time of the pulse wave signal, and may obtain an oscillogram (OW) by plotting the peak-to-peak amplitude at each measurement time against the contact pressure value at a corresponding time and by performing, for example, polynomial curve fitting.

The processor 140 may estimate blood pressure by using the generated oscillogram OW. For example, the processor 140 may estimate mean arterial pressure (MAP) based on contact pressure value MP at a maximum point of the pulse wave in the oscillogram. For example, the processor 140 may determine the contact pressure value MP itself at the maximum point of the pulse wave as MAP. Alternatively, the processor 140 may estimate MAP by applying the contact pressure value MP to a pre-defined MAP estimation equation. In this case, the MAP estimation model may be expressed in the form of various linear or non-linear combination functions, such as addition, subtraction, division, multiplication, logarithmic value, regression equation, and the like, with no particular limitation.

Further, the processor 140 may estimate diastolic blood pressure (DBP) and systolic blood pressure (SBP) based on the contact pressure value MP at the maximum point of the pulse wave, and contact pressure values DP and SP at the left and right points corresponding to amplitude values having a preset ratio (e.g., 0.5 to 0.7) to a maximum amplitude value MA. For example, the processor 140 may determine the contact pressure value MP as MAP, and may determine the contact pressure value DP as DBP and the contact pressure value SP as SBP. Further, by applying each of the extracted contact pressure values MP, DP, and SP to a pre-defined blood pressure estimation model, the processor 140 may estimate MAP, DBP, and SBP independently.

Figure 5:
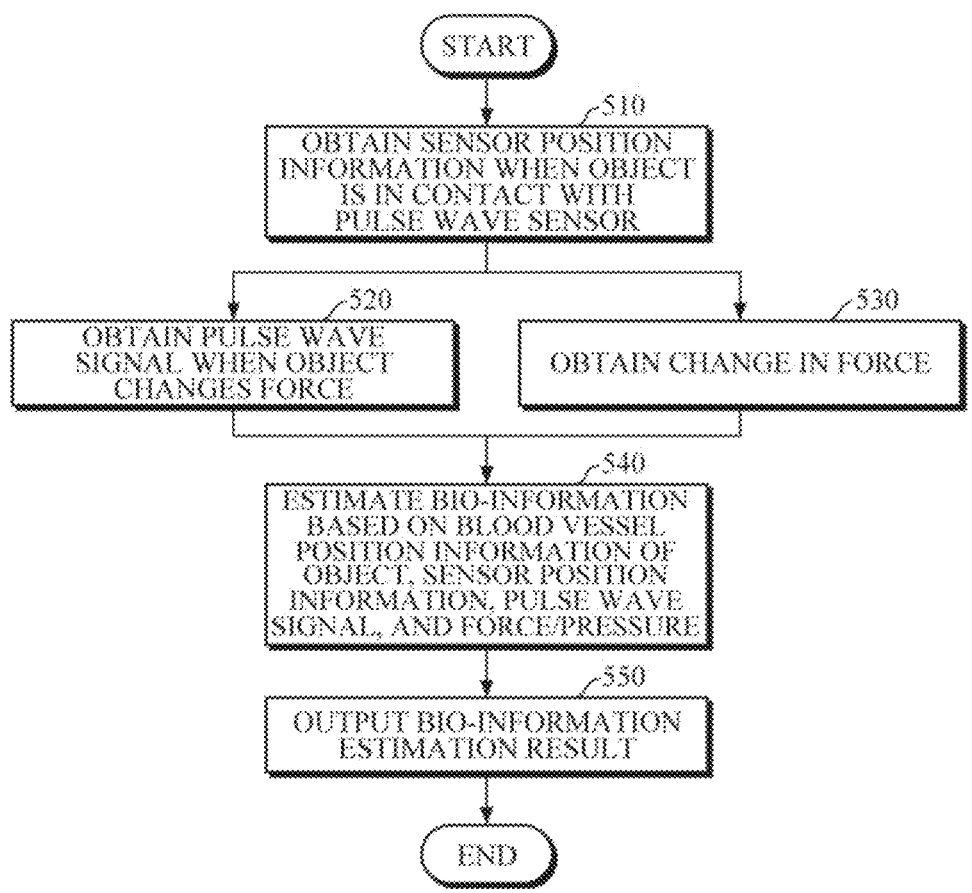
FIG. 5 is a flowchart illustrating a method of estimating bio-information according to an embodiment of the present disclosure.

FIG. 5 is a flowchart illustrating a method of estimating bio-information according to an embodiment of the present disclosure. The method of FIG. 5 is an example of a method of estimating bio-information which is performed by the aforementioned apparatuses 100a and 100b for estimating bio-information. Various embodiments of estimating bio-information are described above in detail, and thus will be briefly described below.

The apparatuses 100a and 100b for estimating bio-information may obtain a position of a pulse wave sensor on an object when the object is in contact with the pulse wave sensor in operation 510. For example, the apparatuses 100a and 100b for estimating bio-information may obtain sensor position information based on an image of the object, captured by an external image capturing device, or a fingerprint image obtained by a fingerprint sensor mounted in the apparatuses.

Based on receiving a request for estimating bio-information from the user, the apparatuses 100a and 100b for estimating bio-information may determine whether there is previous blood vessel position information of the object before performing the operation 510; and if there is no blood vessel position information of the object, the apparatuses 100 and 100b for estimating bio-information may obtain blood vessel position information of the object from the user. For example, the apparatuses 100a and 100b for estimating bio-information may receive input of blood vessel position information from the user, or may obtain blood vessel position information by analyzing an ultrasonic image, an MRI image, and the like, which are obtained from an external device.

Then, the apparatuses 100a and 100b for estimating bio-information may obtain a pulse wave signal when the object, being in contact with the pulse wave sensor, changes force/pressure in operation 520 and, at the same time, may obtain a change in force/pressure in operation 530. In this case, the apparatuses 100a and 100b for estimating bio-information may guide a user on a contact position based on the blood vessel position and the sensor position obtained in operation 510.

Subsequently, the apparatuses 100a and 100b for estimating bio-information may estimate bio-information based on the blood vessel position information of the object, the sensor position information, the pulse wave signal, and the force/pressure in operation 540.

For example, if the pulse wave sensor, having a single channel, obtains one pulse wave signal at a blood vessel position of the object in operation 520, the apparatuses 100a and 100b for estimating bio-information may estimate bio-information using oscillometry based on an amplitude of the pulse wave signal and the force/pressure. Further, if the pulse wave sensor has multiple channels to measure a plurality of pulse wave signals at two or more points of the object, the apparatuses 100a and 100b for estimating bio-information may determine a pulse wave signal, measured by a channel which is located closest to the blood vessel position of the object, among the plurality of pulse wave signals based on the blood vessel position information of the object and the sensor position information, and may estimate bio-information based on the determined pulse wave signal and the force/pressure.

Next, the apparatuses 100a and 100b for estimating bio-information may output a bio-information estimation result in operation 550. The apparatuses 100a and 100b for estimating bio-information may provide a user with information, such as the estimated bio-information values, a warning, measures, a bio-information estimation history, etc., in various manners by using a display, a speaker, a haptic device, and the like.

Figure 6:
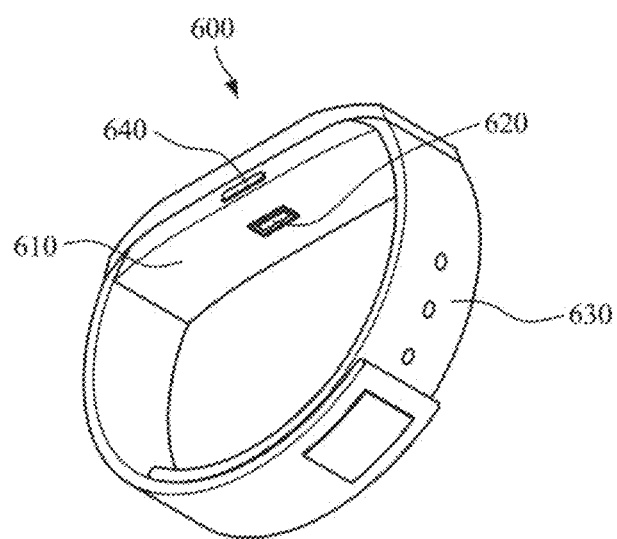
FIG. 6 is a diagram illustrating an example of a wearable device.

FIG. 6 is a diagram illustrating an example of a wearable device. Various embodiments of the aforementioned apparatuses 100a and 100b for estimating bio-information may be mounted in the wearable device.

Referring to FIG. 6, the wearable device 600 includes a main body 610 and a strap 630.

The strap 630, which is connected to both ends of the main body 610, may be flexible so as to be bent around a user's wrist. The strap 630 may be composed of a first strap and a second strap which are separated from each other. Respective ends of the first strap and the second strap are connected to the main body 610, and the other ends thereof may be connected to each other via a connecting means. In this case, the connecting means may be formed as magnetic connection, Velcro connection, pin connection, and the like, but is not limited thereto. Further, the strap 630 is not limited thereto, and may be integrally formed as a non-detachable band.

In this case, air may be injected into the strap 630, or the strap 630 may be provided with an air bladder to have elasticity according to a change in pressure applied to the wrist, and may transmit the change in pressure of the wrist to the main body 610.

A battery may be embedded in the main body 610 or the strap 630 to supply power to the wearable device 600.

The main body 610 may include a sensor part 620 mounted on one side thereof. The sensor part 620 may include a pulse wave sensor for measuring pulse wave signals. The pulse wave sensor may include a light source for emitting light onto skin of a wrist or a finger, a light receiver, such as a CIS optical sensor, a photodiode, etc., which detects light scattered or reflected from the wrist or the finger. The pulse wave sensor may have multiple channels for measuring pulse wave signals at multiple points of the wrist, the finger, etc., and each of the channels may include a light source and a light receiver, or may include a plurality of light sources for emitting light of different wavelengths. In addition, the sensor part 620 may further include a force/pressure sensor for measuring force/pressure between the wrist or finger and the sensor part 620. Furthermore, the sensor part 620 may further include a fingerprint sensor, an ultrasonic sensor, and the like, which may be stacked on top of each other.

A processor may be mounted in the main body 610. The processor may be electrically connected to modules mounted in the wearable device 600. The processor may generate an oscillogram based on the pulse wave signals and the contact force/pressure, which are measured by the sensor part 620, and may estimate blood pressure based on the obtained oscillogram. In this case, the processor may control an output interface to provide information that guides a user regarding a contact position of the object by using pre-defined blood vessel position information of the object and sensor position information when the object is in contact with the sensor part 620, or may determine a channel of a pulse wave sensor, which is located closest to the blood vessel position of the object, and may estimate blood pressure based on the pulse wave signal of the determined channel.

Further, the main body 610 may include a storage which stores reference information for estimating blood pressure and performing various functions of the wearable device 600, and information processed by various modules thereof.

In addition, the main body 610 may include a manipulator 640 which is provided on one side surface of the main body 610, and receives a user's control command and transmits the received control command to the processor. The manipulator 640 may have a power button to input a command to turn on/off the wearable device 600.

Further, a display for outputting information to a user may be mounted on a front surface of the main body 610. The display may have a touch screen for receiving touch input. The display may receive a user's touch input and transmit the touch input to the processor, and may display processing results of the processor.

Moreover, the main body 610 may include a communication interface for communication with an external device. The communication interface may transmit a blood pressure estimation result to the external device, e.g., a user's smartphone.

Figure 7:
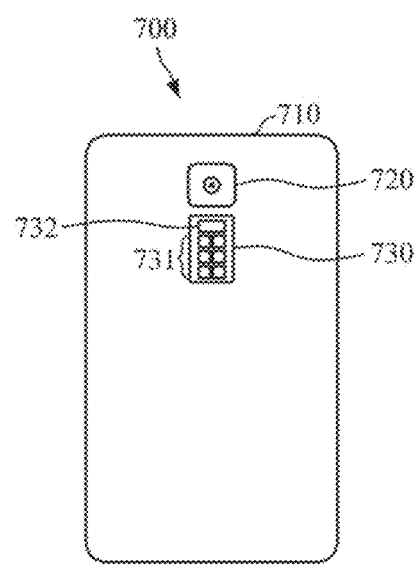
FIG. 7 is a diagram illustrating an example of a smart device.

FIG. 7 is a diagram illustrating an example of a smart device. In this case, the smart device may include a smartphone, a tablet PC, and the like. The smart device may include functions of the aforementioned apparatuses 100a and 100b for estimating bio-information.

Referring to FIG. 7, the smart device 700 includes a main body 710 and a pulse wave sensor 730 mounted on one surface of the main body 710. For example, the pulse wave sensor 730 may include one or more light sources 732 disposed at predetermined positions thereof. The one or more light sources 732 may emit light of different wavelengths. In addition, a plurality of light receivers 731 may be disposed at positions spaced apart from the light sources 732 by a predetermined distance. However, this is merely an example, and the pulse wave sensor 730 may have various shapes as described above. Further, a force/pressure sensor for measuring a contact force/pressure of a finger may be mounted in the main body 710 at a lower end of the pulse wave sensor 730.

Moreover, a display may be mounted on a front surface of the main body 710. The display may visually output a blood pressure estimation result, a health condition evaluation result, and the like. The display may include a touch screen, and may receive information input through the touch screen and transmit the information to a processor.

The main body 710 may include an image sensor 720 as illustrated in FIG. 7. The image sensor 720 may capture various images, and may acquire, for example, a fingerprint image of a finger being in contact with the pulse wave sensor 730. In addition, when an image sensor based on the CIS technology is mounted in the light receivers 731 of the pulse wave sensor 730, the image sensor 720 may be omitted.

As described above, the processor may control an output interface to provide information that guides a user regarding a contact position of an object based on a blood vessel position of the object and sensor position information obtained when the object is in contact with the sensor, or may select one of a plurality of pulse wave signals obtained by a multi-channel pulse wave sensor. The processor may obtain an oscillogram based on the pulse wave signal and force/pressure, and may estimate blood pressure based on the obtained oscillogram.

The example embodiments of the present disclosure can be implemented by computer-readable code written on a non-transitory computer-readable medium, and that is executed by one or more processors. The non-transitory computer-readable medium may be any type of recording device in which data is stored in a computer-readable manner.

Examples of the computer-readable medium include a ROM, a RAM, a CD-ROM, a magnetic tape, a floppy disc, an optical data storage, and a carrier wave (e.g., data transmission through the Internet). The non-transitory computer-readable medium can be distributed over a plurality of computer systems connected to a network so that computer-readable code is written thereto and executed therefrom in a decentralized manner. Functional programs, code, and code segments for implemented the example embodiments of the present disclosure can be readily deduced by programmers of ordinary skill in the art to which the present disclosure pertains.

The present disclosure has been described herein with regard to preferred embodiments. However, it will be obvious to those skilled in the art that various changes and modifications can be made without changing the technical conception of the present disclosure. Thus, it is clear that the above-described embodiments are illustrative in all aspects and are not intended to limit the present disclosure.

What is claimed is:

1. An apparatus for estimating bio-information, the apparatus comprising:
    a pulse wave sensor configured to measure a pulse wave signal from an object;
    a sensor position sensor configured to obtain sensor position information of the pulse wave sensor with respect to the object, based on the object being in contact with the pulse wave sensor;
    a blood vessel position sensor configured to obtain blood vessel position information of the object;
    a processor configured to estimate the bio-information based on the blood vessel position information of the object, the sensor position information, and the pulse wave signal; and
    a display,
    wherein the processor is further configured to control the display to guide a user to place the pulse wave sensor at a blood vessel position of the object based on the blood vessel position information of the object and the sensor position information.

2. The apparatus of claim 1, wherein the sensor position sensor is configured to obtain the sensor position information based on an image of the object, or a fingerprint image.

3. The apparatus of claim 1, wherein the blood vessel position information is based on a user input and at least one of an optical image, an ultrasonic image, a magnetic resonance imaging (MRI) image, and a photoacoustic image of the object.

4. The apparatus of claim 1, wherein the pulse wave sensor has a plurality of channels to measure pulse wave signals at a plurality of points of the object, and
    wherein the processor is further configured to obtain the pulse wave signal for estimating the bio-information by driving at least one of the plurality of channels based on the blood vessel position information of the object and the sensor position information.

5. The apparatus of claim 4, wherein the processor is further configured to determine a channel from among the plurality of channels, which is located closest to a blood vessel position, or a channel which is located within a predetermined distance from the blood vessel position, as the channel to be driven.

6. The apparatus of claim 5, wherein in response to determining that no channel is located within the predetermined distance from the blood vessel position, the processor is further configured to control an output interface to guide a user to change a contact position of the object.

7. The apparatus of claim 1, wherein the pulse wave sensor has a plurality of channels to measure a plurality of pulse wave signals at a plurality of different points of the object or in a predetermined area of the object, and
    wherein the processor is further configured to select at least one pulse wave signal for estimating the bio-information from among the plurality of pulse wave signals, based on the blood vessel position information of the object and the sensor position information.

8. The apparatus of claim 7, wherein the processor is further configured to select the at least one pulse wave signal of a channel which is located closest to the blood vessel position, or the at least one pulse wave signal of a channel which is located within a predetermined distance from the blood vessel position.

9. The apparatus of claim 1, further comprising a force sensor configured to measure a force applied by the object to the pulse wave sensor, or a pressure sensor configured to measure pressure applied by the object to the pulse wave sensor.

10. The apparatus of claim 9, wherein the processor is further configured to estimate the bio-information based on the pulse wave signal, measured by the pulse wave sensor, and the force measured by the force sensor or the pressure measured by the pressure sensor.

11. The apparatus of claim 1, wherein the bio-information comprises one or more of blood pressure, vascular age, arterial stiffness, aortic pressure waveform, vascular compliance, stress index, fatigue level, skin age, and skin elasticity.

12. A method of estimating bio-information, the method comprising:
    based on an object being in contact with a pulse wave sensor, obtaining sensor position information of the pulse wave sensor with respect to the object;
    driving the pulse wave sensor to measure a pulse wave signal from the object;
    obtaining blood vessel position information of the object via a blood vessel position sensor; and
    estimating the bio-information based on blood vessel position information of the object, the sensor position information, and the pulse wave signal;
    displaying information on a display to guide a user to place the pulse wave sensor at a blood vessel position of the object based on the blood vessel position information of the object and the sensor position information.

13. The method of claim 12, wherein the obtaining of the sensor position information comprises obtaining an image of the object by an image sensor based on the object being in contact with the pulse wave sensor, and obtaining the sensor position information based on the image of the object.

14. The method of claim 12, further comprising obtaining the blood vessel position information of the object based on at least one of an ultrasonic image, a magnetic resonance imaging (MRI) image, and a photoacoustic image of the object.

15. The method of claim 12, further comprising measuring a force applied by the object to the pulse wave sensor, or a pressure applied by the object to the pulse wave sensor.

16. The method of claim 15, wherein the estimating of the bio-information comprises estimating the bio-information based on the pulse wave signal, measured by the pulse wave sensor, and the force measured by a force sensor or the pressure measured by a pressure sensor.

17. The method of claim 12, further comprising, in response to a plurality of pulse wave signals being measured at a plurality of points of the object or in a predetermined area of the object, selecting at least one of the plurality of pulse wave signals based on the blood vessel position information of the object and the sensor position information.

18. The method of claim 17, wherein the selecting of the at least one of the plurality of pulse wave signals comprises selecting the at least one of the plurality of pulse wave signals of a channel, which is located closest to the blood vessel position, or the at least one of the plurality of pulse wave signals of a channel which is located within a predetermined distance from the blood vessel position, as the pulse wave signal.

19. An apparatus for estimating bio-information of a user, the apparatus comprising:
    a pulse wave sensor configured to measure a pulse wave signal from an object of the user;
    a sensor position sensor configured to obtain sensor position information of the pulse wave sensor with respect to the object;
    a blood vessel position sensor configured to obtain the blood vessel position information of the object;
    a processor configured to:
        obtain sensor position information that identifies a position of the pulse wave sensor with respect to the object of the user;
        obtain blood vessel position information that identifies a position of a blood vessel of the object of the user; and
    estimate the bio-information of the user based on the pulse wave signal, the sensor position information, and the blood vessel position information, and
    a display, wherein
    the processor is further configured to control the display to guide a user to place the pulse wave sensor at a blood vessel position of the object based on the blood vessel position information of the object and the sensor position information.

* * * * *